US011969422B2

(12) United States Patent
Patel et al.

(10) Patent No.: US 11,969,422 B2
(45) Date of Patent: *Apr. 30, 2024

(54) METHODS OF TREATING HEART FAILURE WITH REDUCED EJECTION FRACTION USING MODIFIED FORMS OF TRIMETAZIDINE

(71) Applicant: IMBRIA PHARMACEUTICALS, INC., Boston, MA (US)

(72) Inventors: Jaikrishna Patel, Cary, NC (US); Paul Chamberlin, Brookline, MA (US)

(73) Assignee: IMBRIA PHARMACEUTICALS, INC., Boston, MA (US)

( * ) Notice: Subject to any disclaimer, the term of this patent is extended or adjusted under 35 U.S.C. 154(b) by 1 day.

This patent is subject to a terminal disclaimer.

(21) Appl. No.: 17/540,638

(22) Filed: Dec. 2, 2021

(65) Prior Publication Data
US 2022/0184062 A1 Jun. 16, 2022

Related U.S. Application Data

(60) Provisional application No. 63/123,728, filed on Dec. 10, 2020.

(51) Int. Cl.
| *A61K 31/496* | (2006.01) |
| *A61K 9/00* | (2006.01) |
| *A61P 9/04* | (2006.01) |

(52) U.S. Cl.
CPC .......... *A61K 31/496* (2013.01); *A61K 9/0053* (2013.01); *A61P 9/04* (2018.01)

(58) Field of Classification Search
CPC ........................... A61K 31/495; A61K 31/496
See application file for complete search history.

(56) References Cited

U.S. PATENT DOCUMENTS

| 4,100,285 | A | * | 7/1978 | Murai | .................. | C07D 251/54 |
| | | | | | | 544/401 |
| 4,166,452 | A | | 9/1979 | Generales, Jr. | | |
| 4,256,108 | A | | 3/1981 | Theeuwes | | |
| 4,265,874 | A | | 5/1981 | Bonsen et al. | | |
| 4,574,156 | A | | 3/1986 | Morita et al. | | |
| 6,214,841 | B1 | | 4/2001 | Jackson et al. | | |
| 10,556,013 | B2 | * | 2/2020 | Levin | ........................ | A61P 9/10 |
| 10,953,102 | B2 | * | 3/2021 | Levin | ..................... | A61K 47/55 |
| 11,376,330 | B2 | * | 7/2022 | Levin | .................... | C07D 213/80 |
| 2003/0232877 | A1 | | 12/2003 | Sikorski et al. | | |
| 2017/0348292 | A1 | | 12/2017 | Kaye | | |
| 2019/0117623 | A1 | | 4/2019 | Simpson, Jr. et al. | | |

FOREIGN PATENT DOCUMENTS

| WO | 2020/081361 A1 | 4/2020 |
| WO | 2020/243119 A1 | 12/2020 |
| WO | 2020/247213 A1 | 12/2020 |

OTHER PUBLICATIONS

Chamberlin, 2021, A Novel First-in Class Partial Fatty Acif Oxidation Inhibitor Improves Cardiac Remodeling and Function Post-Myocardial Infarction, Journal of the American College of Cardiology, 77(18):539.
Egbuche, 2020, Contemporary Pharmacologic Management of Heart Failure with Reduced Ejection Fraction: A Review, Curr Cardiol Rev, 16(1):55-64.
Harding, 2021, ABstract 12092: IMB-1018792, An Investigational Agent Designed to Augment Cardiac Glucose Utilization and Energetics Reduces Cardiac Remodeling and Preserves Cardiac Function in a Model of Pressure Overload-Induced Heart Failure, Metabolism and Physiology, Session Title: Cardiovascular Science, Virtual II, 5 pages.
Hinder, 2018, Developing Drugs for Heart Failure With Reduced Ejection Fraction: What HAve We Learned From Clinical Trials?, Clin Pharmacol Ther, 103(5):802-814.
International Search Report and Written Opinionn issued in International Application No. PCT/ US2021/061583, dated Apr. 21, 2022, 16 pages.
Ma, 2020, Heart failure with preserved ejection fraction: an update on pathophysiology, diagnosis, treatment, and prognosis, Braz J Med Biol Res, 53(7):e9646, 16 pages.
Murphy, 2020, Heart Failure With Reduced Ejection Fraction: A Review, JAMA, 324(5):488-504.
Reed, 2015, A Practical Guide for the Treatment of Symptomatic Heart Failure with Reduced Ejection Fraction (HFrEF), Curr Cardiol Rev, 11(1):23-32.
Sannino, 2009, Biodegradable Cellulose-based Hydrogels: Design and Applications, Materials, 2:353-373.

\* cited by examiner

*Primary Examiner* — Rei Tsang Shiao
(74) *Attorney, Agent, or Firm* — Brown Rudnick LLP; Adam M. Schoen

(57) ABSTRACT

The invention provides methods of treatment of heart failure with reduced ejection fraction (HFrEF) using modified forms of trimetazidine, such as CV-8972 and CV-8814.

18 Claims, No Drawings

METHODS OF TREATING HEART FAILURE WITH REDUCED EJECTION FRACTION USING MODIFIED FORMS OF TRIMETAZIDINE

FIELD OF THE INVENTION

The invention relates to methods of treatment of heart failure with reduced ejection fraction.

BACKGROUND

Estimates of the global incidence of heart failure, the inability of the heart to maintain cardiac output sufficient to meet the body's needs, range from 26 million to 64 million individuals. Heart failure causes shortness of breath and excessive tiredness, which can severely impair quality of life, and 35% of patients with heart failure die within one year of their initial diagnosis. It is estimated that about half of heart failure patients have reduced left ventricular ejection fraction (LVEF), the fraction of blood volume that is ejected from the left ventricle during each contraction. The LVEF of healthy individuals is typically 50-65%, and heart failure patients with a LVEF below 40% are considered to have heart failure with reduced ejection fraction (HFrEF). The five-year survival rate of patients hospitalized with HFrEF is 25%.

Current pharmacological approaches for treating HFrEF include therapies that slow the disease process and those that merely relieve the clinical signs and symptoms of the disease. Therapies in the former category typically include blockers of the renin-angiotensin aldosterone system (RAAS), beta-blockers, or the anti-hypertensive hydralazine, each of which carries the risk of serious side effects. For example, angiotensin converting enzyme inhibitors (ACE-I) and angiotensin receptor blockers, which interfere with RAAS, can cause renal dysfunction, hyperkalemia, and hypotension; beta blockers can cause fatigue and fluid retention; and hydralazine therapy can cause dizziness and headaches. Drugs that relieve symptoms of HFrEF include diuretics, $Na^+/K^+$ ATPase inhibitors, and nitrates, but such drugs have not been shown to improve mortality rates when provided on their own. Moreover, diuretics must be administered carefully because they can activate RAAS and exacerbate the disease. Consequently, current pharmacological therapies for treatment of HFrEF are inadequate, and millions of people with the disease remain limited in their daily lives and at an increased risk of death.

SUMMARY

The invention provides methods of treating HFrEF using modified forms of trimetazidine, such as CV-8972, which has the IUPAC name 2-[4-[(2,3,4-trimethoxyphenyl)methyl]piperazin-1-yl]ethyl pyridine-3-carboxylate and the following structure:

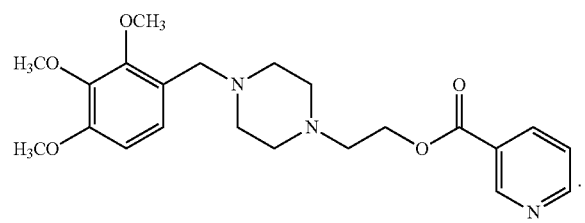

Modified forms of trimetazidine improve cardiac efficiency by shifting cellular metabolism from fatty acid oxidation to glucose oxidation. Unadulterated trimetazidine promotes the use of glucose as a mitochondrial energy source by blocking the activity of long-chain 3-ketoacyl-CoA thiolase, and certain modified forms retain the inhibitory effects but have superior pharmacokinetic properties. CV-8972 also provides a precursor for synthesis of nicotinamide adenine dinucleotide ($NAD^+$), which facilitates mitochondrial respiration to promote mitochondrial ATP production. Thus, CV-8972 stimulates glucose-dependent cardiac energy production via two independent mechanisms. The use of modified forms of trimetazidine provides an alternative to existing pharmacological therapies to mitigate the effects of HFrEF.

In an aspect, the invention provides methods of treating heart failure associated with reduced ejection fraction (HFrEF) in a subject by providing to a subject having HFrEF a compound represented by formula (X):

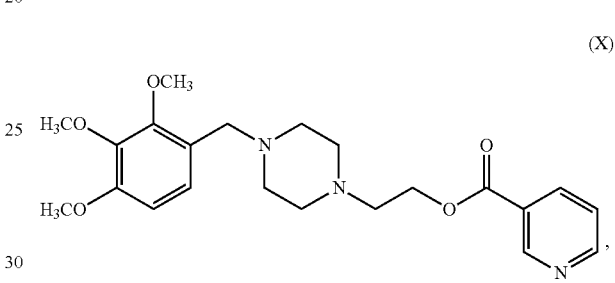

or a pharmaceutically acceptable salt thereof.

In another aspect, the invention provides methods of treating heart failure associated with reduced ejection fraction (HFrEF) in a subject by providing to a subject having HFrEF a compound represented by formula (IX):

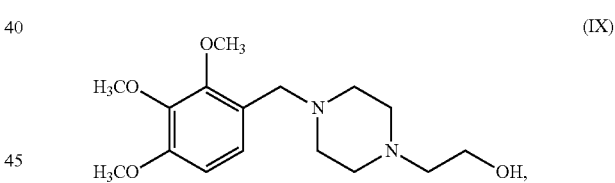

or a pharmaceutically acceptable salt thereof.

The HFrEF may be associated with another condition. The HFrEF may be associated with aortic stenosis, arrhythmia, cerebrovascular accident, chronic obstructive pulmonary disease, cigarette smoking, congenital heart disease, diabetic cardiomyopathy, dilated cardiomyopathy, hypertension, ischemic coronary disease, kidney disease, low baseline left ventricular ejection fraction, low platelet count, male gender, mitral regurgitation, myocardial infarction, myocarditis, obstructive hypertrophic cardiomyopathy, obesity, old age, peripheral vascular disease, renal disease, rheumatic heart disease, valvular disease, or viral myocarditis.

The compound may be provided in a pharmaceutical composition.

The pharmaceutical composition may be provided by any suitable route or mode of administration. The pharmaceutical composition may be administered buccally, by injection, dermally, enterally, intraarterially, intravenously, nasally, orally, parenterally, pulmonarily, rectally, subcutaneously, topically, transdermally, or with or on an implantable medical device (e.g., stent or drug-eluting stent or balloon equivalents).

The pharmaceutical composition may have a format suitable for oral administration. For example, the pharmaceutical composition may be in the form of a tablet, troche, lozenge, aqueous suspension, oily suspension, emulsion, hard capsule, soft capsule, or syrup.

The pharmaceutical composition may contain a mixture of the compound and an erodible polymer that promotes swelling of the mixture in an aqueous environment. The erodible polymer may be hydroxypropyl methylcellulose (HPMC).

The mixture may contain the compound and HPMC in a defined weight ratio. The mixture may contain the compound and HPMC in a weight ratio of about 1:5, about 1:4, about 1:3, about 1:2, about 1:1, about 3:2, about 2:1, about 3:1, about 4:1, about 5:1, from about 1:100 to about 100:1, from about 1:100 to about 50:1, from about 1:100 to about 20:1, from about 1:100 to about 10:1, from about 1:100 to about 5:1, from about 1:100 to about 2:1, from about 1:50 to about 100:1, from about 1:50 to about 50:1, from about 1:50 to about 20:1, from about 1:50 to about 10:1, from about 1:50 to about 5:1, from about 1:50 to about 2:1, from about 1:20 to about 100:1, from about 1:20 to about 50:1, from about 1:20 to about 20:1, from about 1:20 to about 10:1, from about 1:20 to about 5:1, from about 1:20 to about 2:1, from about 1:10 to about 100:1, from about 1:10 to about 50:1, from about 1:10 to about 20:1, from about 1:10 to about 10:1, from about 1:10 to about 5:1, from about 1:10 to about 2:1, from about 1:5 to about 100:1, from about 1:5 to about 50:1, from about 1:5 to about 20:1, from about 1:5 to about 10:1, from about 1:5 to about 5:1, from about 1:5 to about 2:1, from about 1:3 to about 100:1, from about 1:3 to about 50:1, from about 1:3 to about 20:1, from about 1:3 to about 10:1, from about 1:3 to about 5:1, or from about 1:3 to about 2:1.

The pharmaceutical composition may be formulated as a unit dosage containing a defined amount of the compound. The unit dosage may contain about 5 mg, about 10 mg, about 20 mg, about 50 mg, about 100 mg, about 200 mg, about 500 mg, from about 5 mg to about 10 mg, from about 5 mg to about 20 mg, from about 5 mg to about 50 mg, from about 5 mg to about 100 mg, from about 5 mg to about 200 mg, from about 5 mg to about 500 mg, from about 10 mg to about 20 mg, from about 10 mg to about 50 mg, from about 10 mg to about 100 mg, from about 10 mg to about 200 mg, from about 10 mg to about 500 mg, from about 20 mg to about 50 mg, from about 20 mg to about 100 mg, from about 20 mg to about 200 mg, from about 20 mg to about 500 mg, from about 50 mg to about 100 mg, from about 50 mg to about 200 mg, from about 50 mg to about 500 mg, from about 100 mg to about 200 mg, from about 100 mg to about 500 mg, or from about 200 mg to about 500 mg of the compound.

The pharmaceutical composition may contain a specific polymorph of the compound of formula (X). The polymorph may be Form A, Form B, Form C, Form D, or Form E. The pharmaceutical composition may be substantially free of one or more other polymorphs. The composition may include a Form A polymorph and be substantially free of polymorphs of Form B, Form C, Form D, and Form E.

The pharmaceutical composition may include a hydrochloride salt of the compound of formula (X). The pharmaceutical composition may include the compound of formula (X) and the hydrochloride ion in a defined stoichiometric ratio. The pharmaceutical composition may include the compound and the hydrochloride ion in a 1:3 stoichiometric ratio.

The pharmaceutical composition may include a hydrated form of the compound of formula (X). The pharmaceutical composition may include a monohydrate form of the compound. The pharmaceutical composition may include an anhydrous form of the compound.

In another aspect, the invention provides a compound of one of formulas (IX) and (X) for use in treatment of heart failure associated with reduced ejection fraction (HFrEF).

The HFrEF may be associated with another condition, such as any of those described above.

The compound may be provided in a pharmaceutical composition.

The pharmaceutical composition may be provided by a particular route of mode of administration, such as any of those described above.

The pharmaceutical composition may have a format suitable for oral administration, such as any of those described above.

The pharmaceutical composition may contain a mixture of the compound and an erodible polymer that promotes swelling of the mixture in an aqueous environment. The erodible polymer may be hydroxypropyl methylcellulose (HPMC).

The mixture may contain the compound and HPMC in a defined weight ratio, such as any of those described above.

The pharmaceutical composition may be formulated as a unit dosage containing a defined amount of the compound, such as any of the amounts described above.

The pharmaceutical composition may contain a specific polymorph of the compound of formula (X), such as any of those described above.

The pharmaceutical composition may include a hydrochloride salt of the compound of formula (X). The pharmaceutical composition may include the compound of formula (X) and the hydrochloride ion in a defined stoichiometric ratio. The pharmaceutical composition may include the compound and the hydrochloride ion in a 1:3 stoichiometric ratio.

The pharmaceutical composition may include a hydrated form of the compound of formula (X). The pharmaceutical composition may include a monohydrate form of the compound. The pharmaceutical composition may include an anhydrous form of the compound.

DETAILED DESCRIPTION

The invention provides methods of treating heart failure with reduced ejection fraction (HFrEF) using modified forms of trimetazidine. Such drugs improve cardiac efficiency by shifting cellular metabolism from fatty acid oxidation to glucose oxidation, which is a more oxygen-efficient pathway for generating ATP. Trimetazidine promotes the use of glucose as a mitochondrial energy source by blocking the activity of long-chain 3-ketoacyl-CoA thiolase. The modified forms of trimetazidine used in methods of the invention also inhibit thiolase but have superior pharmacokinetic properties. In some methods of the invention, the modified form of trimetazidine includes a precursor for synthesis of nicotinamide adenine dinucleotide (NAD$^+$). NAD$^+$ further improves mitochondrial ATP production by facilitating respiration. By forcing cardiac mitochondria to derive energy from glucose oxidation, the methods of the invention alleviate HFrEF by a different mechanism from prior pharmacological approaches. Thus, they may be used when other therapies are contraindicated or ineffective, or they may be used in combination with other therapies.

HFrEF and Existing Pharmacological Therapies for Treatment of HFrEF

Heart failure is the inability of the heart to maintain cardiac output sufficient to meet the body's needs. Cases of heart failure can be categorized according to the measurement of the left ventricle ejection fraction (LVEF). The LVEF is the volume of blood ejected from the left ventricle with each heartbeat divided by the volume of blood when the left ventricle is maximally filled. Notwithstanding its name, the LVEF is typically expressed as a percentage, and the LVEF in healthy individuals ranges from 50-65%. Consequently, patients with heart failure and a LVEF of at least 50% are considered to have heart failure with preserved ejection fraction (HFpEF). Heart failure patients with a LVEF below 40% are considered to have clinical HFrEF, while those with a LVEF of 40-49% are classified as having heart failure with moderately reduced (or mid-range) ejection fraction (HFmrEF). HFrEF may be accompanied by progressive left ventricular dilatation and adverse cardiac remodeling.

As used herein, HFrEF includes any heart failure patients with a LVEF below 50%, i.e., the term encompasses the clinical definitions of both HFrEF and HFmrEF, unless otherwise stated. Thus, within the context of this application, HFrEF may include a subject that has heart failure and a LVEF of less than about 50%, less than about 49%, less than about 48%, less than about 47%, less than about 46%, less than about 45%, less than about 44%, less than about 43%, less than about 42%, less than about 41%, or less than about 40%.

Existing pharmacological approaches to thwart the progress of HFrEF focus on inhibition of one or both of the renin-angiotensin aldosterone system (RAAS) and the sympathetic nervous system (SNS). Drugs that inhibit the RAAS include angiotensin converting enzyme inhibitors (ACE-Is), such as benazepril, captopril, enalapril, fosinopril, lisinopril, moexipril perindopril, quinapril, ramipril, and trandolapril; angiotensin receptor blockers (ARBs), such as azilsartan, candesartan, eprosartan, irbesartan, losartan, olmesartan, telmisartan, and valsartan; and aldosterone antagonists, such as eplerenone and spironolactone; and anti-hypertensives, such as hydralazine and sacubitril. Drugs that inhibit the SNS include beta blockers, such as acebutolol, atenolol, bisoprolol, carvedilol, metoprolol, nadolol, nebivolol, and propranolol. Other drugs or drug classes of drugs that have also been used to treat HFrEF include aspirin; statins, such as atorvastatin, fluvastatin, lovastatin, pitavastatin, pravastatin, rosuvastatin, and simvastatin; omega polyunsaturated fatty acids, such as alpha-linolenic acid, docosahexaenoic acid, and eicosapentaenoic acid; and anticoagulants, such as acenocoumarol, anisindione, apixaban, brodifacoum, chlorophacinone, coumatetralyl, dabigatran, dicoumarol, diphacinone, fluindione, phenindione, phenprocoumon, pindone, rivaroxaban, and tioclomarol; and antiarrhythmics, such as amiodarone, dofetilide, and mexiletine;

Current pharmacotherapies to treat HFrEF also includes agents that relieve symptoms but do not slow disease progress. Examples symptom-relieving drugs include diuretics, such as bumetanide, chlorthalidone, furosemide, hydrochlorothiazide, indapamide, metolazone, and torasemide (torsemide); nitrates, such as glyceryl trinitrate, isosorbide dinitrate, and isosorbide mononitrate; and Na$^+$/K$^+$ ATPase inhibitors, such as digoxin and digitoxin.

Current therapies also include the use of combinations of the aforementioned drugs from different categories. For example, the combination of sacubitril and valsartan is licensed as an angiotensin receptor-neprilysin inhibitor (ARNI).

The diagnosis, treatment, and prognosis of HFrEF are described in, for example, Brent N Reed and Carla A Sueta, A Practical Guide for the Treatment of Symptomatic Heart Failure with Reduced Ejection Fraction (HFrEF), Curr Cardiol Rev. 2015 February; 11(1): 23-32, doi: 10.2174/1574884708666131117125508; Chao Ma, et al., Heart failure with preserved ejection fraction: an update on pathophysiology, diagnosis, treatment, and prognosis, Braz J Med Biol Res. 2020 Jun. 5; 53(7):e9646, doi: 10.1590/1414-431X20209646; Egbuche 0, et al., Contemporary Pharmacologic Management of Heart Failure with Reduced Ejection Fraction: A Review, Curr Cardiol Rev. 2020; 16(1): 55-64, doi: 10.2174/1573403X15666190709185011; Markus Hinder, et al., Developing Drugs for Heart Failure With Reduced Ejection Fraction: What Have We Learned From Clinical Trials? Clin Pharmacol Ther. 2018 May; 103(5): 802-814, doi: 10.1002/cpt.1010, Murphy SP, et al., Heart Failure With Reduced Ejection Fraction: A Review, JAMA. 2020 Aug. 4; 324(5):488-504, doi: 10.1001/jama.2020.10262, the contents of each of which are incorporated herein by reference.

HFrEF has a variety of causes and risk factors linked to the disease. For example and without limitation, HFrEF may result from, or be associated with, aortic stenosis, arrhythmia, cerebrovascular accident, chronic obstructive pulmonary disease, cigarette smoking, congenital heart disease, diabetic cardiomyopathy, dilated cardiomyopathy, hypertension, ischemic coronary disease, kidney disease, low baseline left ventricular ejection fraction, low platelet count, male gender, mitral regurgitation, myocardial infarction, myocarditis, obstructive hypertrophic cardiomyopathy, obesity, old age, peripheral vascular disease, renal disease, rheumatic heart disease, valvular disease, or viral myocarditis.

Modified Forms of Trimetazidine

Methods of the invention include the use of modified forms of trimetazidine. Trimetazidine has the following structure:

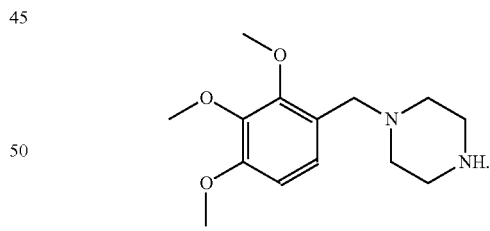

Trimetazidine is described as the first cytoprotective anti-ischemic agent developed and has long been used to treat angina.

Trimetazidine promotes glucose oxidation by inhibiting oxidation of fatty acids. Glucose oxidation and fatty acid oxidation are energy-producing metabolic pathways that compete with each other for substrates. In glucose oxidation, glucose is broken down to pyruvate via glycolysis in the cytosol of the cell. Pyruvate then enters the mitochondria, where it is converted to acetyl coenzyme A (acetyl-CoA). In beta-oxidation of fatty acids, which occurs in the mitochondria, two-carbon units from long-chain fatty acids are sequentially converted to acetyl-CoA. The remaining steps in energy production from oxidation of glucose or fatty acids are common to the two pathways. Briefly, they include breakdown of acetyl-CoA to carbon dioxide via the citric acid cycle, the concomitant generation of a proton gradient across the mitochondrial inner membrane via a series of oxygen-dependent electron transport reactions, and the use of the energy potential in the proton gradient to drive ATP synthesis. Trimetazidine inhibits oxidation of fatty acids by blocking long-chain 3-ketoacyl-CoA thiolase, thus causing cells to rely on glucose oxidation to support energy production.

Forcing cardiac mitochondria to rely on oxidation of glucose rather fatty acids as an energy source provides a therapeutic benefit for many patients with cardiovascular conditions. In certain types of heart disease, the overall efficiency of energy production by cardiac mitochondria is diminished due in part to an increased reliance on fatty acid oxidation over glucose oxidation. Glucose oxidation is a more efficient pathway for energy production, as measured by the number of ATP molecules produced per $O_2$ molecule consumed, than is fatty acid oxidation. Thus, overall cardiac efficiency can be increased by agents that promote glucose oxidation, such as trimetazidine.

CV-8972 was recently identified as a trimetazidine-derivative having improved pharmacological properties. CV-8972 has the IUPAC name 2-[4-[(2,3,4-trimethoxyphenyl)methyl]piperazin-1-yl]ethyl pyridine-3-carboxylate and the structure of formula (X):

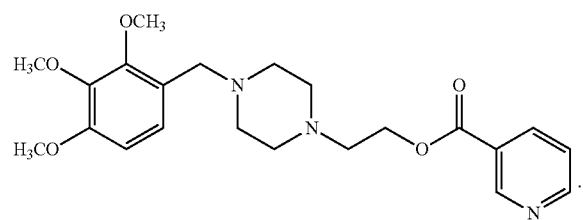

(X)

When CV-8972 is administered to a subject, it is initially broken into nicotinic acid and CV-8814, which has the IUPAC name 244-[(2,3,4-trimethoxyphenyl)methyl]piperazin-1-yflethanol and the structure of formula (IX):

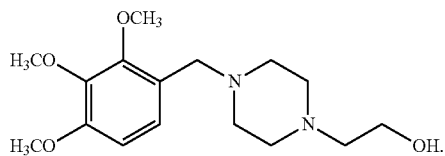

(IX)

CV-8814 is a hydroxyethyl derivative of trimetazidine, and the hydroxyethyl group is subsequently removed in the body to provide trimetazidine. CV-8972 and its metabolic products are described in U.S. Pat. No. 10,556,013, the contents of which are incorporated herein by reference.

The improved therapeutic properties of CV-8972 are due in part to the effect of nicotinic acid. Nicotinic acid serves as a precursor for synthesis of nicotinamide adenine dinucleotide ($NAD^+$), the oxidized form of an essential coenzyme in the mitochondrial electron transport reaction. Supplying a $NAD^+$ precursor ensures that mitochondrial redox reactions occur robustly to drive ATP synthesis, regardless of whether oxidation of glucose or fatty acids is used to feed the citric acid cycle. Thus, the nicotinic acid product of CV-8972 promotes mitochondrial respiration.

The stepwise breakdown of CV-8972 to CV-8814 and then to trimetazidine also contributes to the improved therapeutic properties of CV-8972. Like trimetazidine, CV-8814 inhibits 3-ketoacyl-CoA thiolase, so CV-8972 delivers two different glucose-shifting active pharmaceutical ingredients (APIs). However, CV-8814 does not produce the same undesirable side effects as trimetazidine. In addition, due to the sequential metabolism of CV-8972, the level of circulating trimetazidine following a dose of CV-8972 is much lower than the level following of comparable dose of trimetazidine itself. Therefore, compared to unadulterated trimetazidine, CV-8972 provides a more sustained level of circulating API and fewer side effects.

Other modified forms of trimetazidine that may be used in compositions of the invention are described in, for example, U.S. Pat. Nos. 4,100,285 and 4,574,156, the contents of each of which are incorporated herein by reference.

Modified forms of trimetazidine, such as the compounds described above, may include one or more atoms that are enriched for an isotope. For example, the compounds may have one or more hydrogen atoms replaced with deuterium or tritium. Isotopic substitution or enrichment may occur at carbon, sulfur, or phosphorus, or other atoms. The compounds may be isotopically substituted or enriched for a given atom at one or more positions within the compound, or the compounds may be isotopically substituted or enriched at all instances of a given atom within the compound.

Pharmaceutical Compositions

Methods of the invention may include providing a modified form of trimetazidine, such as one of the compounds described above, in a pharmaceutical composition. The composition may be formulated for any route or mode of administration. For example and without limitation, the composition may be formulated for buccal, dermal, enteral, intraarterial, intramuscular, intraocular, intravenous, nasal, oral, parenteral, pulmonary, rectal, subcutaneous, topical, or transdermal administration. The composition may be formulated for administration by injection or with or on an implantable medical device (e.g., stent or drug-eluting stent or balloon equivalents).

A pharmaceutical composition containing one or more the compounds may be in a form suitable for oral use, for example, as tablets, troches, lozenges, fast-melts, aqueous or oily suspensions, dispersible powders or granules, emulsions, hard or soft capsules, syrups or elixirs.

Compositions intended for oral use may be prepared according to any method known in the art for the manufacture of pharmaceutical compositions and such compositions may contain one or more agents selected from sweetening agents, flavoring agents, coloring agents and preserving agents, in order to provide pharmaceutically elegant and palatable preparations. Tablets contain the compounds in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated, or they may be coated by known techniques to delay disintegration in the stomach and absorption lower down in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,166,452 and 4,265,874, to form osmotic therapeutic tablets for control release. Preparation and administration of compounds is discussed in U.S. Pat. No. 6,214,841 and U.S. Patent Publication No. 2003/0232877, incorporated by reference herein in their entirety.

Formulations for oral use may also be presented as hard gelatin capsules in which the compounds are mixed with an inert solid diluent, for example calcium carbonate, calcium phosphate or kaolin, or as soft gelatin capsules in which the compounds are mixed with water or an oil medium, for example peanut oil, liquid paraffin or olive oil. An alternative oral formulation, where control of gastrointestinal tract hydrolysis of the compound is sought, can be achieved using a controlled-release formulation, where a compound of the invention is encapsulated in an enteric coating.

Aqueous suspensions may contain the compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents such as a naturally occurring phosphatide, for example lecithin, or condensation products of an alkylene oxide with fatty acids, for example, polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the compounds in a vegetable oil, for example, arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the compounds in admixture with a dispersing or wetting agent, suspending agent and one or more preservatives. Suitable dispersing or wetting agents and suspending agents are exemplified, for example sweetening, flavoring and coloring agents, may also be present.

Pharmaceutical compositions may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavoring agents.

Syrups and elixirs may be formulated with sweetening agents, such as glycerol, propylene glycol, sorbitol or sucrose. Such formulations may also contain a demulcent, a preservative, and agents for flavoring and/or coloring. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be in a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Pharmaceutical compositions may contain mixtures that include erodible polymers that promote swelling of the mixture in an aqueous environment. Pharmaceutical compositions that contain CV-8972 and one or more erodible polymers are described in co-owned Application Nos. 63/046,115 and 63/046,117. An erodible polymer is any polymer that breaks down inside the body within a physiologically relevant time frame. The erodible polymer may have other characteristics that promote the gradual release of the modified form of trimetazidine from the mixture. For example and without limitation, the polymer may be one or more of the following: biocompatible, i.e., not harmful to living tissue; hydrophilic; hygroscopic; tending to form a hydrogel.

Without wishing to be bound by theory, the polymer-containing mixtures may promote gradual release by one or more mechanisms. For example, swelling of the mixture by absorption of water may facilitate diffusion of the modified form of trimetazidine from the mixture. Degradation of the polymer may also allow the modified form of trimetazidine to be released from the mixture. Osmotic pressure due the high concentration gradient of compound between the inside and outside of the mixture may also contribute to diffusion of the modified form of trimetazidine from the mixture.

For example and without limitation, the polymer may be a cellulose derivative, a gelatin derivative, e.g., a cross-linked gelatin derivative, or a polyester derivative.

Derivatives of cellulose, is a linear chain β(1→4) linked D-glucose units, include polymers that contain substitutions on one of more of the hydroxyl groups of each glucose unit. Substituents may be organic or inorganic and are typically attached via ester or ether linkages. Cellulose ester derivatives include carboxymethyl cellulose (CMC), e.g., sodium carboxymethyl cellulose, ethyl cellulose, ethyl hydroxyethyl cellulose, ethyl methyl cellulose, hydroxyethyl cellulose, hydroxyethyl methyl cellulose, hydroxypropyl cellulose (HPC), hydroxypropyl methylcellulose (HPMC), and methylcellulose. Cellulose ether derivatives include cellulose acetate, cellulose acetate butyrate, cellulose acetate propionate, cellulose propionate, cellulose sulfate, cellulose triacetate, and nitrocellulose. The use of cellulose-based polymers to form biodegradable hydrogels is known in the art and described in, for example, Sannino, et al., Biodegradable Cellulose-based Hydrogels: Design and Applications, Materials 2009, 2, 353-373; doi:10.3390/ma2020353, the contents of which are incorporated herein by reference.

The mixture may contain multiple polymers or multiple polymeric forms of the same polymer. For example, HPMC polymeric forms may differ in a variety of physical properties, including viscosity, degree of methoxyl substitution, degree of hydroxypropoxyl substitution, or average molecule weight.

The viscosity of a H1VIPC polymeric form may be determined by testing under standard conditions, including the concentration of HMPC in the solution and the temperature of the solution. For example and without limitation, the HPMC concentration may be 1%, 1.5%, 2%, 2.5%, or 3%. For example and without limitation, the temperature of the solution may be 15° C., 16° C., 17° C., 18° C., 19° C., 20° C., 21° C., 22° C., 23° C., 24° C., or 25° C.

A polymeric form of a cellulose derivative, such as HPMC, may have a defined viscosity. For example and without limitation, a polymeric form of HPMC may have a viscosity of from about 2 cP to about 4 cP, from about 4 cP to about 6 cP, from about 5 cP to about 8 cP, from about 12 cP to about 18 cP, from about 40 cP to about 60 cP, from about 80 cP to about 120 cP, from about 300 cP to about 500 cP, from about 1200 cP to about 2400 cP, from about 2500 cP to about 5000 cP, from about 9000 cP to about 18,000 cP, from about 12,000 cP to about 24,000 cP, from about 12,000 cP to about 24,000 cP, from about 75,000 cP to about 150,000 cP, at least about 2 cP at least about 4 cP at least about 5 cP at least about 12 cP at least about 40 cP at least about 80 cP at least about 300 cP at least about 1200 cP at least about 2500 cP at least about 9000 cP at least about 12,000 cP at least about 12,000 cP at least about 75,000 cP less than about 4 cP, less than about 6 cP, less than about 8 cP, less than about 18 cP, less than about 60 cP, less than about 120 cP, less than about 500 cP, less than about 2400 cP, less than about 5000 cP, less than about 18,000 cP, less than about 24,000 cP, less than about 24,000 cP, or less than about 150,000 cP for a 2% aqueous solution of the polymeric form at 20° C.

Polymeric forms of cellulose derivatives, such as HPMC, may vary in their degree of substitution of the glucose units. The degree of substitution may be expressed as a weight percentage of the substituent or as a molar ratio of substituent to glucose unit. For a cellulose derivative that has two different substituents, such as HPMC, the polymeric form may be described by the degree of substitution for each substituent.

Each polymeric form of HPMC may independently have a defined degree of methoxyl substitution. For example and without limitation, the degree of methoxyl substitution may be from about 19% to about 24%, from about 22% to about 24%, from about 27% to about 30%, from about 27% to about 30%, or from about 28% to about 32%.

Each polymeric form of HPMC may independently have a defined degree of hydroxypropoxyl substitution. For example and without limitation, the degree of hydroxypropoxyl substitution may be from about 4% to about 8%, from about 7% to about 10%, from about 7% to about 12%, from about 8% to about 10%, from about 8% to about 11%, or from about 9% to about 12%.

Each polymeric form of HPMC may independently have a defined average molecular weight. The average molecular weight may be about 10 kDa, about 13 kDa, about 20 kDa, about 26 kDa, about 41 kDa, about 63 kDa, about 86 kDa, about 110 kDa, about 120 kDa, about 140 kDa, about 180 kDa, or about 220 kDa.

When multiple forms of a polymer, such as HPMC, are present, one or more polymeric forms may be present in a defined amount. For example and without limitation, a polymer, such as HPMC, may contain about 50%, about 60%, about 70%, about 80%, about 90%, about 95%, about 96%, about 97%, about 98%, about 99%, at least 50%, at least 60%, at least 70%, at least 80%, at least 90%, at least 95%, at least 96%, at least 97%, at least 98%, or at least 99% by weight of one polymeric form.

Pharmaceutical compositions may contain a crystal form of a modified form of trimetazidine, such as CV-8972. As described in co-owned U.S. Application No. 63/046,120, CV-8972 may exist in at least five polymorphic forms: Form A, Form B, Form C, Form D, and Form E. A pharmaceutical composition may contain one polymorph of CV-8972 and be substantially free of one or more other polymorphs. For example, the composition may include a Form A polymorph and be substantially free of polymorphs of Form B, Form C, Form D, and Form E.

A composition containing a polymorph of CV-8972 may be substantially free of one or more other polymorphic forms of CV-8972 if the composition contains the predominant polymorph at a defined level of purity. Purity may be expressed as the amount of predominant polymorph as a percentage of the total weight of two of more polymorphs of CV-8972.

In certain embodiments, the total weight is the weight of all polymorphs of CV-8972 in the composition. For example, a composition that contains the Form A polymorph and is substantially free of other polymorphs may contain Form A at a defined weight percentage of all polymorphs of CV-8972 in the composition. For example, the composition may contain Form A at at least 95% by weight, at least 96% by weight, at least 97% by weight, at least 98% by weight, at least 99% by weight, at least 99.5% by weight, at least 99.6% by weight, at least 99.7% by weight, at least 99.8% by weight, or at least 99.9% by weight of all polymorphs of CV-8972 in the composition.

In certain embodiments, the total weight is the weight of selected polymorphs of CV-8972 in the composition. For example, a composition that contains the Form A polymorph and is substantially free of the Form B polymorph may contain Form A at a defined weight percentage of Forms A and B. For example, the composition may contain Form A at at least 95% by weight, at least 96% by weight, at least 97% by weight, at least 98% by weight, at least 99% by weight, at least 99.5% by weight, at least 99.6% by weight, at least 99.7% by weight, at least 99.8% by weight, or at least 99.9% by weight of Forms A and B of CV-8972 in the composition. Similarly, a composition that contains the Form A polymorph and is substantially free of the Form B and C polymorphs may contain Form A at a defined weight percentage of Forms A, B, and C. For example, the composition may contain Form A at at least 95% by weight, at least 96% by weight, at least 97% by weight, at least 98% by weight, at least 99% by weight, at least 99.5% by weight, at least 99.6% by weight, at least 99.7% by weight, at least 99.8% by weight, or at least 99.9% by weight of Forms A, B, and C of CV-8972 in the composition.

Alternatively or additionally, a composition containing a polymorph of CV-8972 may be substantially free of one or more other polymorphic forms of CV-8972 if the composition contains the secondary polymorphs at levels below a defined level. Presence of a secondary polymorphs may be defined as the amount of one or more secondary polymorphs as a percentage of the total weight of two of more polymorphs of CV-8972.

In certain embodiments, the total weight is the weight of all polymorphs of CV-8972 in the composition. For example, a composition that contains the Form A polymorph and is substantially free of other polymorphs may contain all polymorphs other than Form A at a defined weight percentage of all polymorphs of CV-8972 in the composition. For example, the composition may contain all polymorphs other than Form A at below 5% by weight, below 4% by weight, below 3% by weight, below 2% by weight, below 1% by weight, below 0.5% by weight, below 0.4% by weight, below 0.3% by weight, below 0.2% by weight, or below 0.1% by weight of all polymorphs of CV-8972 in the composition.

In certain embodiments, the total weight is the weight of selected polymorphs of CV-8972 in the composition. For example, a composition that contains the Form A polymorph and is substantially free of the Form B polymorph may contain Form B at a defined weight percentage of Forms A and B. For example, the composition may contain Form B at below 5% by weight, below 4% by weight, below 3% by weight, below 2% by weight, below 1% by weight, below 0.5% by weight, below 0.4% by weight, below 0.3% by weight, below 0.2% by weight, or below 0.1% by weight of Forms A and B of CV-8972 in the composition. Similarly, a composition that contains the Form A polymorph and is substantially free of the Form B and Form C polymorphs may contain Forms B and C at a defined weight percentage of Forms A, B, and C. For example, the composition may contain Forms B and C at below 5% by weight, below 4% by weight, below 3% by weight, below 2% by weight, below 1% by weight, below 0.5% by weight, below 0.4% by weight, below 0.3% by weight, below 0.2% by weight, or below 0.1% by weight of Forms A, B, and C of CV-8972 in the composition.

The crystal may contain a salt form of CV-8972. For example, the Form A polymorph CV-8972 is a trihydrochloride salt. Thus, the composition may include CV-8972 and the chloride ion a defined stoichiometric ratio. The composition may include CV-8972 and the chloride ion in a 1:3 stoichiometric ratio.

The crystal may contain a hydrated form of CV-8972. For example, the Form A polymorph CV-8972 is a monohydrate. Thus, the composition may include a monohydrate form of CV-8972, such as the Form A polymorph. The composition may include an anhydrous form of CV-8972, such as a Form B, Form D, or Form E polymorph.

The pharmaceutical composition may be formulated as a single unit dosage. The pharmaceutical composition may be formulated as divided dosages.

The composition may contain a defined dose of CV-8972 or CV-8814. The dose may contain from about 10 mg to about 2000 mg, from about 10 mg to about 1000 mg, from about 10 mg to about 800 mg, from about 10 mg to about 600 mg, from about 10 mg to about 400 mg, from about 10 mg to about 300 mg, from about 10 mg to about 200 mg, from about 25 mg to about 2000 mg, from about 25 mg to about 1000 mg, from about 25 mg to about 800 mg, from about 25 mg to about 600 mg, from about 25 mg to about 400 mg, from about 25 mg to about 300 mg, about 25 mg to about 200 mg, from about 50 mg to about 2000 mg, from about 50 mg to about 1000 mg, from about 50 mg to about 800 mg, from about 50 mg to about 600 mg, from about 50 mg to about 400 mg, from about 50 mg to about 300 mg, about 50 mg to about 200 mg, from about 100 mg to about 2000 mg, from about 100 mg to about 1000 mg, from about 100 mg to about 800 mg, from about 100 mg to about 600 mg, from about 100 mg to about 400 mg, from about 100 mg to about 300 mg, from about 100 mg to about 200 mg, from about 200 mg to about 2000 mg, from about 200 mg to about 1000 mg, from about 200 mg to about 800 mg, from about 200 mg to about 600 mg, from about 200 mg to about 400 mg, from about 200 mg to about 300 mg, from about 300 mg to about 2000 mg, from about 300 mg to about 1000 mg, from about 300 mg to about 800 mg, from about 300 mg to about 600 mg, or from about 300 mg to about 400 mg of CV-8972 or CV-8814. The dose may contain about 10 mg, about 25 mg, about 50 mg, about 100 mg, about 200 mg, about 300 mg, or about 400 mg of CV-8972 or CV-8814.

Providing a Compound to a Subject

The invention provides methods of treating HFrEF in a subject by providing a modified form of trimetazidine, such as one of the compounds described above. The compound may be provided by any suitable route or mode of administration. For example and without limitation, the compound may be provided buccally, dermally, enterally, intraarterially, intramuscularly, intraocularly, intravenously, nasally, orally, parenterally, pulmonarily, rectally, subcutaneously, topically, transdermally, by injection, or with or on an implantable medical device (e.g., stent or drug-eluting stent or balloon equivalents).

The modified form of trimetazidine may be provided according to a dosing regimen. A dosing regimen may include a dosage, a dosing frequency, or both. Doses may be provided at any suitable interval. For example and without limitation, doses may be provided once per day, twice per day, three times per day, four times per day, five times per day, six times per day, eight times per day, once every 48 hours, once every 36 hours, once every 24 hours, once every 12 hours, once every 8 hours, once every 6 hours, once every 4 hours, once every 3 hours, once every two days, once every three days, once every four days, once every five days, once every week, twice per week, three times per week, four times per week, or five times per week.

The dose may contain a defined amount of CV-8972 or CV-8814 that improves cardiac mitochondrial function, such as any of the doses described above in relation to pharmaceutical compositions containing CV-8972 or CV-8814.

The dose may be provided in a single dosage, i.e., the dose may be provided as a single tablet, capsule, pill, etc. Alternatively, the dose may be provided in a divided dosage, i.e., the dose may be provided as multiple tablets, capsules, pills, etc.

The dosing may continue for a defined period. For example and without limitation, doses may be provided for at least one week, at least two weeks, at least three weeks, at least four weeks, at least six weeks, at least eight weeks, at least ten weeks, at least twelve weeks or more.

The subject may be a human that has HFrEF. The subject may be a pediatric, a newborn, a neonate, an infant, a child, an adolescent, a pre-teen, a teenager, an adult, or an elderly subject. The subject may be in critical care, intensive care, neonatal intensive care, pediatric intensive care, coronary care, cardiothoracic care, surgical intensive care, medical intensive care, long-term intensive care, an operating room, an ambulance, a field hospital, or an out-of-hospital field setting.

The invention includes combination therapies in which a modified form of trimetazidine is provided to a subject in combination with a second agent, such as any of the drugs described above in the section on HFrEF. The modified form of trimetazidine and the second agent may be provided in a single composition, or they may be provided in separate compositions. The modified form of trimetazidine and the second agent may be provided according to the same dosing regimen, or they may be provided according to different dosing regimens.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification, and guidance that can be adapted to the practice of this invention in its various embodiments and equivalents thereof.

What is claimed is:

1. A method of treating heart failure associated with reduced ejection fraction (HFrEF) in a subject, the method comprising providing to a subject having HFrEF a compound represented by formula (X):

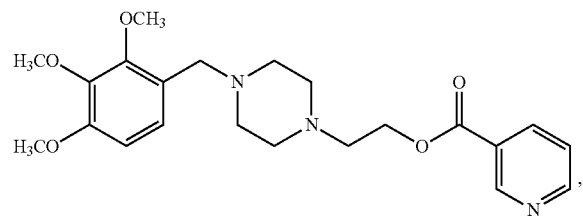 [SMILES: COc1ccc(CN2CCN(CCOC(=O)c3cccnc3)CC2)c(OC)c1OC]

or a pharmaceutically acceptable salt thereof.

2. The method of claim 1, wherein the HFrEF is associated with a condition selected from the group consisting of aortic stenosis, arrhythmia, cerebrovascular accident, chronic obstructive pulmonary disease, cigarette smoking, congenital heart disease, diabetic cardiomyopathy, dilated cardiomyopathy, hypertension, ischemic coronary disease, kidney disease, low baseline left ventricular ejection fraction, low platelet count, male gender, mitral regurgitation, myocardial infarction, myocarditis, obstructive hypertrophic cardiomyopathy, obesity, old age, peripheral vascular disease, renal disease, rheumatic heart disease, valvular disease, and viral myocarditis.

3. The method of claim 1, wherein the compound is provided in a pharmaceutical composition.

4. The method of claim 3, wherein the pharmaceutical composition is provided orally.

5. The method of claim 4, wherein the composition comprises a format selected from the group consisting of a tablet, troche, lozenge, aqueous suspension, oily suspension, emulsion, hard capsule, soft capsule, and syrup.

6. The method of claim 3, wherein the pharmaceutical composition comprises a mixture of the compound and an erodible polymer that promotes swelling of the mixture in an aqueous environment.

7. The method of claim 6, wherein the erodible polymer is hydroxypropyl methylcellulose (HPMC).

8. The method of claim 7, wherein the mixture comprises the compound and HMPC in a ratio of from about 1:10 to about 10:1.

9. The method of claim 3, wherein the pharmaceutical composition is a unit dosage comprising from about 10 mg to about 500 mg of the compound.

10. A method of treating heart failure associated with reduced ejection fraction (HFrEF) in a subject, the method comprising providing to a subject having HFrEF a compound represented by formula (IX):

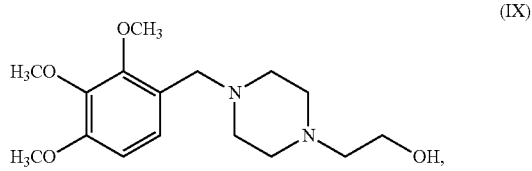 [SMILES: COc1ccc(CN2CCN(CCO)CC2)c(OC)c1OC]

or a pharmaceutically acceptable salt thereof.

11. The method of claim 10, wherein the HFrEF is associated with a condition selected from the group consisting of aortic stenosis, arrhythmia, cerebrovascular accident, chronic obstructive pulmonary disease, cigarette smoking, congenital heart disease, diabetic cardiomyopathy, dilated cardiomyopathy, hypertension, ischemic coronary disease, kidney disease, low baseline left ventricular ejection fraction, low platelet count, male gender, mitral regurgitation, myocardial infarction, myocarditis, obstructive hypertrophic cardiomyopathy, obesity, old age, peripheral vascular disease, renal disease, rheumatic heart disease, valvular disease, and viral myocarditis.

12. The method of claim 10, wherein the compound is provided in a pharmaceutical composition.

13. The method of claim 12, wherein the pharmaceutical composition is provided orally.

14. The method of claim 13, wherein the composition comprises a format selected from the group consisting of a tablet, troche, lozenge, aqueous suspension, oily suspension, emulsion, hard capsule, soft capsule, and syrup.

15. The method of claim 12, wherein the pharmaceutical composition comprises a mixture of the compound and an erodible polymer that promotes swelling of the mixture in an aqueous environment.

16. The method of claim 15, wherein the erodible polymer is hydroxypropyl methylcellulose (HPMC).

17. The method of claim 16, wherein the mixture comprises the compound and HMPC in a ratio of from about 1:10 to about 10:1.

18. The method of claim 12, wherein the pharmaceutical composition is a unit dosage comprising from about 10 mg to about 500 mg of the compound.

* * * * *